United States Patent
Keenan et al.

(10) Patent No.: US 6,770,285 B2
(45) Date of Patent: Aug. 3, 2004

(54) HYDROPHOBIC OIL ABSORBING POLYMERS AND PROCESS

(75) Inventors: Andrea C. Keenan, Plymouth Meeting, PA (US); Willie Lau, Spring House, PA (US); Curtis Schwartz, Ambler, PA (US)

(73) Assignee: Rohm and Haas Company, Philadelphia, PA (US)

(*) Notice: Subject to any disclaimer, the term of this patent is extended or adjusted under 35 U.S.C. 154(b) by 94 days.

(21) Appl. No.: 09/990,037

(22) Filed: Nov. 20, 2001

(65) Prior Publication Data

US 2002/0061322 A1 May 23, 2002

Related U.S. Application Data

(60) Provisional application No. 60/253,370, filed on Nov. 28, 2000.

(51) Int. Cl.[7] .................................................. A61K 7/00
(52) U.S. Cl. ................... 424/401; 424/70.1; 424/78.18; 526/64; 526/304; 526/328; 510/475; 510/576; 510/476
(58) Field of Search ................. 424/401, 70.1, 424/78.18; 526/64, 304, 328; 510/475, 516, 476

(56) References Cited

U.S. PATENT DOCUMENTS

| 4,880,842 A | 11/1989 | Kowalski et al. ............. 521/64 |
| 4,940,578 A | 7/1990 | Yoshihara et al. ............ 424/70 |
| 5,521,266 A | 5/1996 | Lau ............................. 526/200 |
| 5,641,847 A | 6/1997 | Hozumi et al. ............. 526/328 |
| 6,040,409 A * | 3/2000 | Lau et al. .................... 526/328 |

FOREIGN PATENT DOCUMENTS

| EP | 0 295 903 B1 | 6/1988 |
| EP | 0441512 | 8/1991 |

OTHER PUBLICATIONS

XP–002189672, Abstract of J06182199 A, 19940705, "Oil Absorbing Material—consists of support of oil–permeating material which is loaded with specific polymer particles".

* cited by examiner

Primary Examiner—Thurman K. Page
Assistant Examiner—Lakshmi Channavajjala
(74) Attorney, Agent, or Firm—Stephen E. Johnson

(57) ABSTRACT

Hydrophobic, oil-absorbing polymeric compositions, prepared from high levels of hydrophobic monomers, are provided for transferring oily substances and hydrophobic materials to and from various surfaces in a heterogeneous medium. A reversible process is described for transferring oily substances and hydrophobic materials to and from various surfaces in a heterogeneous medium using oil-absorbing films, solid particles or dispersions of aqueous emulsion polymers prepared from hydrophobic monomers.

19 Claims, No Drawings

HYDROPHOBIC OIL ABSORBING POLYMERS AND PROCESS

CROSS REFERENCE TO RELATED PATENT APPLICATIONS

This is a non-provisional application of prior pending U.S. provisional application serial No. 60/253,370 filed Nov. 28, 2000.

The present invention relates to hydrophobic, oil-absorbing polymeric compositions for transferring oily substances and hydrophobic materials to and from various surfaces in a heterogeneous medium. In particular, the invention is directed to a reversible process for transferring oily substances and hydrophobic materials from various surfaces in a heterogeneous medium using oil-absorbing films, solid particles or dispersions of aqueous emulsion polymers prepared from hydrophobic monomers.

The removal of oils, greases, protein based stains and odors from textiles, fabrics, hard surfaces, skin, pharmaceuticals, animal products, liquids, air and the environment using a single class of polymeric materials is desirable. In addition, the removal or transfer of such materials from surfaces in a heterogeneous medium is also desired. Oil-absorbing polymeric materials are broadly divided into two classes, one class comprising synthetic high-molecular weight polymers and the other class comprising naturally occurring polymeric materials. Examples of the former class of materials are polypropylene, polystyrene, polyurethane foam, polymethyl(meth)acrylate, and polyacrylic acid. Examples of the latter class of materials are pulp fibers, cotton fibers, cellulose, modified celluloses, starches, dextrins and gums. However, materials from both classes have a somewhat narrow range of oil-absorbing efficiencies and/or limited capacities to function as oil-absorbing materials, which is due in part to polymer composition and to the physical form of the material. For example, it is difficult to achieve the physical combination of an oil-absorbing solid suspended in water with an oily substance soaked in to a substrate, such as a fabric, with the result that the oily substance is transferred in the heterogeneous medium to the solid.

U.S. Pat. No. 4,940,578 and European publication EP 0 295 903 disclose a hair preparation comprising a squalene-absorbing, polymeric composition prepared from a vinyl monomer which helps to reduce the greasiness of hair and scalp. However, there remains a need for alternative polymeric materials which have superior oil absorbing properties, both for naturally occurring oils and synthetic oils, and which is effective at removing oily substances from textiles, hard surfaces, oil/water emulsions, multiphasic media and other environments. Moreover, polymeric materials having the ability to absorb oily substances as well as providing a means for transporting them from various surfaces in a heterogeneous medium are still sought. A process using an oil-absorbing polymeric composition for the removal of oils and greases from surfaces would, therefore, be of great utility to the commercial manufacture of detergents, cosmetics, cleaners, personal care products and environmental oil-absorbing materials.

The inventors have discovered, surprisingly, a class of polymer compositions prepared from hydrophobic monomers that facilitate the removal of oily substances and hydrophobic materials in a heterogeneous medium beyond the capability of current oil-absorbing polymer compositions. A hydrophobic, oil-absorbing polymer composition has been discovered that has the ability to absorb at least 20 weight percent of an oily substance or hydrophobic material based on the total weight of the polymeric composition. In adddition, the inventors have discovered reversible processes, using the hydrophobic polymer compositions, for removing, transferring or transporting oily substances and hydrophobic materials from a variety of substrates and surfaces in a heterogeneous medium.

In a first aspect of the present invention there is provided an oil-absorbing polymer composition of Formula 1:

Formula 1

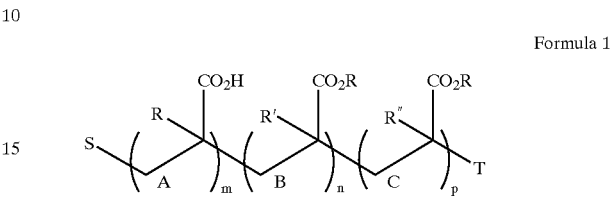

wherein A is a polymerized residue of (meth)acrylic acid; B is a polymerized residue of a monomer selected from one or more $C_8$–$C_{24}$ alkyl (meth)acrylates; C is a residue of a monomer selected from one or more $C_1$–$C_{24}$ alkyl (meth) acrylates; and wherein the polymer composition, in the form of solid particles, a film or a dispersion, absorbs at least 20 weight percent of an oily substance or hydrophobic material in a heterogeneous medium based on the total weight of the polymeric composition.

In a second aspect of the present invention there is provided a process for removing an oily substance or hydrophobic material from a surface of a substrate in a heterogeneous medium including the steps of directly contacting the surface of the substrate containing an oily substance with the oil absorbing polymer composition, in the form of solid particles, a film or a dispersion; allowing the polymer composition to absorb the oily substance or hydrophobic material; and removing the swollen oil-containing polymer composition from the medium.

In a third aspect of the present invention there is provided a process for removing an oily substance or hydrophobic material from a substrate in a heterogeneous medium including the steps of combining a substrate containing an oily substance, the oil-absorbing polymer composition in the form of a dispersion and, optionally, a carrier composition or complexation agent to facilitate transport in the medium; allowing the polymer composition to absorb the oily substance or hydrophobic material; and separating the swollen oil-containing polymer composition from the medium.

The oil-absorbing polymer composition usefully employed in accordance with the present invention is prepared from a combination of an ionic monomer and one or more hydrophobic monomers, which results in a polymer composition having the formula:

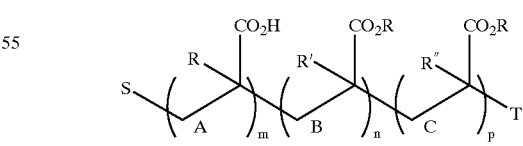

wherein A is a polymerized residue of (meth)acrylic acid; B is a polymerized residue of a monomer selected from one or more $C_8$–$C_{24}$ alkyl (meth)acrylates; C is a residue of a monomer selected from one or more $C_1$–$C_{24}$ alkyl (meth) acrylates. "Polymerized residue" refers to monomer units A, B and C. A, B and C residues are randomly arranged in said polymer. S and T represent initiators and chain transfer residues, respectively. R represents H, $CH_3$ or an alkyl group. The term "m" represents the total number of A residues and ranges from 1 to 20, preferably 1 to 5, most preferably 1 to 3. The preferred weight percent of monomer units of A ranges from to 0.01 to 5. The term "n" represents the total number of B residues and is >1. The preferred weight percent of monomer units of B ranges from to 5–95, depending on the weight percent of monomer units of C. The term "p" represents the total number of C residues and is >1. The preferred weight percent of monomer units of C ranges from to 5–95, depending on the weight percent of monomer units of B.

The oil-absorbing polymer composition is prepared as a terpolymer although compositions containing more than three monomer residues are contemplated. In a preferred embodiment, the oil-absorbing polymer composition, usefully employed in accordance with the present invention, is a terpolymer, wherein monomer A is a residue of (meth) acrylic acid, monomer B is a residue selected from $C_8$–$C_{20}$ alkyl (meth)acrylates, and monomer C is residue selected from $C_1$–$C_{24}$ alkyl (meth)acrylates, S and T represent initiators and chain transfer residues, respectively. In another preferred embodiment, the oil-absorbing polymer composition is a terpolymer, wherein monomer A is a residue of (meth)acrylic acid, monomer B is a residue selected from $C_{12}$–$C_{20}$ alkyl (meth)acrylate monomer, and monomer C is methyl (meth)acrylate, S and T represent initiators and chain transfer residues, respectively. The terpolymer is prepared from relatively high levels (as wt %) of hydrophobic monomers and relatively low levels (as wt %) of ionic monomers in the form of (meth)acrylic acid or acrylic acid in a wide range of weight average molecular weight, $M_w$. The terpolymer includes from 80% to 98% by weight of a combination of hydrophobic monomers in the form of $C_4$–$C_{24}$ alkyl (meth)acrylates and from 0.01% to 20% by weight of ionic monomers. Preferably, the terpolymer includes from 90% to 99.99% by weight of a combination of hydrophobic monomers in the form of $C_4$–$C_{24}$ alkyl (meth)acrylates and from 0.01% to 10% by weight of ionic monomers in the form (meth)acrylic acid. More preferably, the terpolymer includes up to 98% by weight of a combination of hydrophobic monomers in the form of $C_4$–$C_{24}$ alkyl (meth)acrylates and from 1% to 3% by weight of (meth)acrylic acid. The term "alkyl (meth)acrylate" refers to either the corresponding acrylate or methacrylate ester. Similarly, the term "(meth) acrylic" refers to either acrylic acid or methacrylic acid and its corresponding derivatives, such as esters or amides.

The weight average molecular weight of the backbone, as measured on the polymer product after exhaustive hydrolysis, consisting of polymerized units of A, B and C, ranges from 300 to 600,000. Preferably, weight average molecular weights range from 1000 to 100,000. In terms of oil-absorbing capacity, oil-absorbing polymer compositions having weight average molecular weights ranging from 100,000 to 600,000 are preferred. In terms of removing and transporting the swollen oil-containing polymer composition from a heterogeneous medium, oil-absorbing polymer compositions having weight average molecular weights ranging from 300 to 100,000 are preferred. Weight average molecular weights were measured using gel permeation chromatography (GPC) with styrene as a standard and are expressed as weight average molecular weight.

Monomers suitable for the oil-absorbing polymer composition and its use in the novel processes of the present invention include hydrophobic and ionic monoethylenically unsaturated monomers which can be subjected to free radical polymerization in a straight forward manner using standard emulsion polymerization techniques. "Ionic monomers" refer to monoethylenically unsaturated monomers which are water soluble under the conditions of emulsion polymerization, as described in U.S. Pat. No. 4,880,842. As used herein, the term "water soluble", as applied to monomers, indicates that the monomer has a solubility of at least 1 gram per 100 grams of water, preferably at least 10 grams per 100 grams of water and more preferably at least about 50 grams per 100 grams of water. "Hydrophobic monomers" refer to monoethylenically unsaturated monomers which have low or very low water solubility under the conditions of emulsion polymerization, as described in U.S. Pat. No. 5,521,266. As used herein, monomers having "low water solubility" or "very low water solubility" refers to monoethylenically unsaturated monomers having a water solubility at 25–50° C. of no greater than 200 millimoles/ liter water or 50 millimoles/liter water, respectively, and the hydrophobic monomers employed in this invention are monomers having low water solubility. The resulting oil-absorbing polymer compositions that are employed in this invention have low to very low water solubility. The advantages of both the oil-absorbing polymer and its use in the novel processes of the invention are realized when the oil-absorbing polymer composition includes relatively large amounts of hydrophobic monomers compared to relatively small amounts of ionic monomers.

Suitable monomer units of A are ionic monomers that include monoethylenically unsaturated mono carboxylic acids such as for example, acrylic acid (AA), methacrylic acid (MAA), alpha-ethacrylic acid, β,β-dimethyl acrylic acid, vinyl acetic acid, allyl acetic acid and alkali and metal salts thereof. Methacrylic acid is preferred.

Suitable monomer units of B and C are hydrophobic monomers that include one or more $C_1$–$C_{24}$ alkyl (meth) acrylates or $C_1$–$C_{24}$ alkyl acrylates. Suitable alkyl (meth) acrylates or alkyl acrylates include for example methyl (meth)acrylate, ethyl acrylate (EA), isopropyl (meth) acrylate, butyl acrylate(BA), butyl (meth)acrylate (BMA), 2-ethyl hexyl acrylate, benzyl (meth)acrylate, octyl acrylate, decyl acrylate, lauryl acrylate, behenyl acrylate, lauryl (meth)acrylate (LMA), oleyl (meth)acrylate, palmityl (meth)acrylate, stearyl (meth)acrylate (SMA), behenyl (meth)acrylate, cetyl(meth)acrylate, eicosyl(meth)acrylate; blends of $C_{10}$–$C_{24}$ alkyl (meth)acrylates, such as cetyl-eicosyl (meth)acrylate (CEMA); aromatic and alkyl aromatic esters of (meth)acrylic acid; and unsaturated vinyl esters of (meth)acrylic acid such as those derived from fatty acids and fatty alcohols and combinations thereof. Preferably, monomer units of B are lauryl (meth)acrylate, oleyl (meth)acrylate, palmityl (meth)acrylate, behenyl (meth)acrylate, stearyl (meth)acrylate, cetyl(meth)acrylate, eicosyl(meth)acrylate. Preferably, monomer units of C are methyl(meth)acrylate, ethyl acrylate (EA), isopropyl (meth) acrylate, butyl acrylate, butyl (meth)acrylate, 2-ethyl hexyl acrylate, benzyl (meth)acrylate, octyl acrylate, decyl (meth) acrylate, behenyl (meth)acrylate and lauryl (meth)acrylate.

The oil-absorbing emulsion polymers compositions usefully employed in accordance with the present invention are prepared from relatively high levels of hydrophobic monomers and relatively low levels ionic monomers using the methods described in U.S. Pat. Nos. 4,797,223; 4,404,309;

5,008,329, 5,521,266; 6,040,409 6,063,857 and European publication EP 0 989 163 A1. The process for preparing an aqueous emulsion, oil-absorbing polymer of this invention includes providing one or more hydrophobic, ethylenically unsaturated monomers, an ionic monomer and a free radical redox initiator system under emulsion polymerization conditions. The preparation of blends of two or more oil-absorbing polymers are also usefully employed in accordance with the present invention.

In another aspect of the present invention the oil-absorbing polymer composition may be prepared by a multistage emulsion polymerization process, in which at least two stages differing in composition are polymerized in sequential fashion. Such a process usually results in the formation of at least two mutually incompatible polymer compositions, thereby resulting in the formation of at least two phases within the polymer particles. Such particles are composed of two or more phases of various geometries such as, for example, core/shell or core/sheath particles, core/shell particles with shell phases incompletely encapsulating the core, core/shell particles with a multiplicity of cores, and interpenetrating network particles. In all of these cases the majority of the surface area of the particle will be occupied by at least one outer phase and the interior of the particle will be occupied by at least one inner phase. Each of the stages of the multi-staged emulsion polymer may contain the same monomers, surfactants, chain transfer agents, etc. as disclosed herein-above for the emulsion polymer. The polymerization techniques used to prepare such multistage emulsion polymers are well known in the art such as, for example, U.S. Pat. Nos. 4,325,856; 4,654,397; and 4,814,373.

S and T residues are derived from one or more initiator radicals and one or more chain transfer agents, respectively, as described in U.S. Pat. No. 5,521,266. Optionally, groups capable of undergoing cross-linking reactions may be grafted onto the backbone via a radical reaction. A free radical initiator or redox initiator (S) is used in the aqueous solution and emulsion polymerizations. Suitable free radical initiators include for example hydrogen peroxide; tert-butyl hydroperoxide; t-amyl hydroperoxide; sodium, potassium, lithium and ammonium persulfate. Suitable reducing agents include for example bisulfite and its salts, metabisulfite and its salts, sodium formaldehyde sulfoxylate and reducing sugars such as ascorbic acid may be used in combination with the initiar to form a redox system. The amount of initiator may be from 0.01% by weight to about 2% by weight of the monomer charged and in a redox system, a corresponding range of 0.01% by weight to about 2% by weight of a reducing agent may be used. Optionally, transition metal catalysts, such as iron salts, may be used. Typical chain transfer agents (T) having high or low water solubility include for example hydrophobic mercaptans, such as n-dodecyl mercaptan; thiophenol; hydrophobic polymercaptans; hydrophobic halogen compounds, such as bromotrichloromethane and the like or mercaptoethanol and aminoethylenethiol.

Surfactants and organic solvents may be present during the polymerization of the ionic and hydrophobic monomers used to prepare the oil-absorbing polymer composition. It is preferred the oil-absorbing polymer compositions are prepared without the use of organic solvents or high levels of surfactants. Moreover, the oil-absorbing, hydrophobic polymer compositions are prepared from high levels of hydrophobic monomers in the presence of a complexation agent or phase transfer agent. Suitable complexation or phase transfer agents include for example α-cyclodextrin, β-cyclodextrin, γ-cyclodextrin and cyclodextrin derivatives such as methyl-β-cyclodextrin, crown ethers, and the like.

The oil-absorbing polymer composition may include cross-linking agents to build polymer molecular weight and to produce modified polymer structures/conformations. Suitable cross-linking agents include for example allyl (meth)acrylate, ethylene glycol di(meth)acrylate (EGDMA), butylene glycol di(meth)acrylate (BGDMA), methylene bisacrylamide, pentaerythritol, di-, tri- and tetra-acrylates, divinyl benzene, polyethylene glycol diacrylates and bisphenol A diacrylates.

The oil-absorbing emulsion polymer compositions of the present invention have an average particle diameter that ranges from 20 nm to 1000 nm, preferably from 100 nm to 600 nm. Particle sizes herein are those determined using a Brookhaven Model BI-90 particle sizer manufactured by Brookhaven Instruments Corporation, Holtsville N.Y., and polymer particle diameters are reported as "effective diameter. Also contemplated are multimodal particle size oil absorbing emulsion polymers wherein two or more distinct particle sizes of or very broad distributions are provided as described in U.S. Pat. Nos. 5.340,858; 5,350,787; 5,352,720; 4,539,361 and 4,456,726.

The oil-absorbing polymer compositions of the present invention may be used as prepared (in slightly acidic form) or the acidic groups (~1 to 3%) may be neutralized to form salts containing carboxylate anions. Preferred alkali metal ions typically include sodium or potassium, alkaline earth metal cations such as magnesium and calcium, ammonium or tetra-alkyl ammonium salts, such as tetra methyl ammonium, or organic amine salts, such as the salts of tri-$C_1$–$C_4$ alkyl amines, hydroxy ethyl amines, or the mono-, di- or tri-$C_1$–$C_4$-alkanolamines, or mixtures thereof.

The oil-absorbing polymer composition usefully employed in accordance with the present invention may be used in the form of a solid, such as a spray dried or freeze dried powder, granules or film, and in liquid form as a water-borne latex dispersion. The oil absorbing polymer composition may be co-granulated or formulated with an inorganic carrier. Suitable examples of an inorganic carrier include for example alkali metal silicates, carbonates, sulfates, aluminosilicates and phosphates. Preferably, the polymer composition is usefully employed as an aqueous or co-solvent based dispersion.

In a second aspect of the present invention there is provided a process for removing an oily substance or hydrophobic material from a surface of a substrate in a heterogeneous medium including the steps of directly contacting the surface of the substrate containing an oily substance with the oil-absorbing polymer composition, in the form of solid particles, a film or a dispersion; allowing the oil-absorbing polymer composition to absorb the oily substance or hydrophobic material; and removing the swollen oil-containing polymer composition from the medium. "Heterogeneous medium" refers to any closed system having two or more different phases of matter or two or more immiscible solvents in a liquid phase. Heterogeneous media include, but are not limited to for example a water-oil emulsion, an oil-water emulsion, a solid substrate containing a oily substance or hydrophobic material in water, an aqueous latex dispersion of the oil absorbing polymer composition and a solid substrate, a solid substrate saturated with an oily substance in water, any aqueous cleaning system employing the oil-absorbing polymer, any dry cleaning system employing the oil-absorbing polymer, any solvent based cleaning system, any cosmetic delivery system such as a polymer strip, compacted powder, and microsponge, any surface cleaning system employing the oil-absorbing polymer, any filtration system employing the oil-absorbing polymer, any bi-phasic extraction system, any organic compound dispersed in water or a solvent and any multi-component or multi-phase solvent system.

Direct contact of the oil-absorbing emulsion polymer composition usefully employed in the process of the invention with the oily surface can be effected with the composition in one of several forms in the following way including for example i) directly applying a neutralised solution containing the oil-absorbing polymer to the oily substrate surface; ii) directly applying the oil-absorbing polymer as prepared to the oily substrate surface; iii) contacting the oily substrate surface with a neutralised or as supplied solution of the oil-absorbing polymer; iv) contacting the oily substrate surface with the oil-absorbing composition in the form of a film; and v) contacting the oily substrate surface with the oil-absorbing composition in the form of freezed-dried or solid particles. Direct contact refers to any means of applying the oil-absorbing polymer to the oily substrate surface including for example coating, dabbing, spraying sponging, wiping and dipping in a pre-soaking surface treatment.

Through direct contact, the oily substance or hydrophobic material is apparently transferred from the substrate to the oil-absorbing polymer causing the oily substance or hydrophobic material to swell in to the oil-absorbing polymer to afford an oil-containing emulsion polymer composition. The process is reversible in that the oil-containing emulsion polymer composition can transport or release the oily substance or hydrophobic material to the surface of a different substrate. Transport may be effected by for example a complexation agent such as a cyclodextrin while release or transfer may be effected by for example a mechanical force, diffusion, and mechanical agitation.

Oily substances or hydrophobic materials effectively transported or removed from substrates using the oil-absorbing polymer process include for example body oils such as sebum and squalene, proteins, protein containing substances such as food, blood, fat; lipids, fatty acids, waxes, mineral oils, silicone oils, motor oils, crude oils, organic compounds, lipophilic toxins such as PCB, pesticides, insecticides, and herbicides; greases and vegetable oils. The oil-absorbing polymer process has utility in transferring or removing oily substances from surfaces of substrates including for example textiles, fabric, hard surfaces such as ceramics, wood, tile asphalt, cement; human skin, animal skin. Moreover, the oil-absorbing polymer compositions can be usefully combined or formulated with detergents such as those used in the home, industrially or in the environment; cleaners, personal care products such as hair and body washes and cosmetics, medical or pharmaceutical products.

In a third aspect of the present invention there is provided a process for removing an oily substance or hydrophobic material from a substrate in a heterogeneous medium including the steps of combining a substrate containing an oily substance, the oil-absorbing polymer composition in the form of a dispersion and, optionally, a carrier composition or complexation agent to facilitate transport in the medium; allowing the oil-absorbing polymer composition to absorb the oily substance or hydrophobic material; and separating the swollen oil-containing polymer composition from the medium.

The process usefully employed with this aspect of the invention includes combining the oil-absorbing polymer composition with another composition including for example a cleaner such as a detergent, a personal care product such as a cosmetic and a filtration system such as an air filter so that the oil-absorbing polymer contacts the substrate surface in the heterogeneous medium through an indirect process. The process also includes impregnating the oil-absorbing polymer composition on a carrier, which includes, but is not limited to, plastics sheets, cosmetic strips, fibers, textiles, filter materials and paper products.

The novel oil-absorbing polymer compositions and processes have utility in a wide variety of products including, but not limited to, for example household products such as laundry spot pre-treatments in the form of liquids, gels, solid sticks and spray-on, liquid and powder laundry detergents, dish washing and automatic dishwasher detergents, laundry bars, general purpose hard surface cleaners, floor cleaners, oven cleaners, odor control products, carpet/upholstery cleaners; personal care products such as microsponges or polyethylene sheets for facial oil removal, anti-aging skin care, anti-wrinkle cream, shampoos, hair washes, hair treatments, hair preparations, skin treatments, skin preparations, body washes, liquid and bar facial soaps, acne cleansing pads and general purpose cleaning pads or wipes, moisturizing creams, lotions and foundations, deodorants in body oils and odor absorbents, silicon replacements, makeup and foundations to absorb or release natural oils; medical and pharmaceutical products; extraction of toxins, absorption, transportation and release of hydrophobic materials; industrial products such as filtration systems for air and water, cleansing and odor control, (cigarette filters), floor coatings for non or low gloss, matte finish floors, (tiles, stones and non resilient substrates), general and floor cleaning in apartments, hospitals, hotels, restaurants and commercial businesses, environmental oil spills and toxic waste clean up of finely dispersed materials, vehicle and transportation cleaner/garage oil spill clean up, pitch control in paper machines to remove organic impurities, oil production-removal of residual oil contaminant, oil drilling fluids, food extraction (cholesterol from eggs), and paper products to hold or absorb printer ink (non-smudging).

The following examples illustrate specific aspects and particular embodiments of the invention which, however, are not to be construed as limited thereby. The following abbreviations are used in the examples:

| | |
|---|---|
| SMA | stearyl (meth)acrylate |
| LMA | lauryl (meth)acrylate |
| MMA | methyl (meth)acrylate |
| MAA | (meth)acrylic acid |
| BA | butyl acrylate |
| STY | styrene |
| CTA | chain transfer agent |
| XL | cross-linking agent |
| Mw | weight average molecular weight |
| p.s. | particle size |

TABLE I

Oil Absorbing Latex Compositions

| Example No. | SMA | LMA | MMA | MAA | BA | STY | CTA | XL | Mw | Tg °C. | p.s. nm |
|---|---|---|---|---|---|---|---|---|---|---|---|
| E1 | 93 | | 5 | 2 | | | 0 | | >550,000 | −53 | 152 |
| E2 | 93 | | 5 | 2 | | | 3 | | 11,800 | −53 | 178 |
| E3 | 93 | | 5 | 2 | | | 7 | | 5800 | −53 | 183 |
| E4 | 93 | | 5 | 2 | | | 10 | | 4000 | −53 | 200 |
| E5 | 93 | | 5 | 2 | | | 10 | | Dialyzed | −53 | 200 |
| E6 | 93 | | 5 | 2 | | | 10 | 0.25 | 10,000 | −53 | 200 |
| E7 = 3:1E1:E4 | 93 | | 5 | 2 | | | blend | | blend | | |
| E8 = 1:3 E1:E4 | 93 | | 5 | 2 | | | blend | | blend | | |
| E9 | | 45 | 43 | 2 | 10 | | 10 | | | 15.5 | 166 |
| E10 | | | | 2 | 80 | 18 | 10 | | | −28.8 | 160 |
| E11 | | | 46.7 | 1.3 | 52 | | | | | | |
| E12 | 46 | 47 | 5 | 2 | | | | | | | |
| E13 | 46 | 47 | 5 | 2 | | | | 0.5 | | | |
| E14 | 93 | | 5 | 2 | | | | 0.2 | | −53 | 160 |

Monomer components and CTA components are expressed as weight %. Particle size was measured by light scattering. Polymer compositions were prepared by emulsion polymerization techniques as described in U.S. Pat. No. 5,521,266. Examples E10 and E11 were prepared by standard emulsion polymerization techniques. Weight average molecular weights were measured using GPC with styrene as a standard and are expressed as weight average molecular weight.

TABLE II

Oil Absorption Controls

| Control No. | Name | Composition | p.s. |
|---|---|---|---|
| C1 | Zeolite Valfor ™ 100 | Aluminum Silicate | |
| C2 | Zeolite MAP ™ | Aluminum Silicate | |
| C3 | Bentonite Clay | Aluminum Silicate | |
| C4 | EGL-300 ™ | Poly(divinylbenzene) | 30 micron |
| C5 | Polytrap ™ 6603 | LMA/Glycol dimethacrylate crosspolymer | 10–40 micron |
| C6 | Polytrap ™ 7100 | LMA/Glycol DMA plus dimethicone | |
| C7 | Oletran ™ | Triclosan | |
| C8 | PDR-137A ™ | Acrylic polymer | |
| C9 | C-1000/C18 GC packing | C18/MMA column packing material | |
| C10 | Paraloid ™ 9902-XP | LMA/STY/BA/MAA with MMA/BA shell | 250 nm |
| C11 | Aldrich ™ p(LMA) | p(LMA-coethylene glycol DMA) | >1 micron |

Oil-absorbing polymer compositions and controls are summarised in Tables I and II, respectively. Table III summarises oil absorption data for the oil-absorbing polymer compositions of the invention and controls. Oil absorption was measured as described in the publication, British International Standard ISO 787/5. Freeze-dried polymers were used in the oil absorption experiments. Known amounts (0.25 g to 2.0 g) of the freeze-dried polymers were weighed out on glass slides. Various oils were added dropwise until an endpoint was determined. Endpoint refers to a fluid paste state, unless otherwise noted. Oil absorption values (OAV) were expressed as the volume of oil (mls) absorbed per gram of polymer, further expressed as a percentage. A range of OAV was determined for varying amounts of a specific polymer composition.

TABLE III

Oil Absorption Data for Polymer Compositions and Controls

| Example | Squalene | Olive Oil | Oleo/milk | Syn Sebum | Rate of Oil Absorption | Time | Comments |
|---|---|---|---|---|---|---|---|
| E1 | 200–285 | 275–300 | 610–640 | 325–360 | slow | 2–3 min. | gelled complex |
| E2 | 275–290 | 310–320 | 460–470 | 350–360 | moderate | 1–1.5 min. | |
| E3 | 290–300 | 260–290 | 400–410 | 300–310 | moderate | 1–1.5 min. | |
| E4 | 50–75 | 130–145 | 470–500 | 300–310 | fast | 5–30 sec. | smooth fluid paste |
| E5 | 100–136 | 100–133 | | | fast | 5–30 sec. | |
| E6 | 286–300 | 260–266 | | | fast | 5–30 sec. | |
| E7 | 230–245 | 250–260 | | | slow | 2–3 min. | |
| E8 | 130–150 | 190–200 | | | slow | 2–3 min. | |
| E9 | | 120–135 | | | fast | 5–30 sec. | |

TABLE III-continued

Oil Absorption Data for Polymer Compositions and Controls

| Example | Squalene | Olive Oil | Oleo/milk | Syn Sebum | Rate of Oil Absorption | Time | Comments |
|---|---|---|---|---|---|---|---|
| E10 | | 40–50 | 160–175 | | fast | 5–30 sec. | |
| C1 | 108–178 | 112–130 | | | fast | 5–30 sec. | |
| C2 | 161–167 | 200–205 | | | fast | 5–30 sec. | gritty |
| C3 | 143–158 | 160–175 | | | slow | 2–3 min. | |
| C4 | 337–342 | 385–435 | | | fast | 5–30 sec. | |
| C5 | 1140–1180 | 1500–1580 | | | moderate | 1–1.5 min. | sl gritty |
| C6 | 317–342 | 158–200 | | | slow | 2–3 min. | coats, not absorbed |
| C7 | 99–100 | 128–133 | | | moderate | 1–1.5 min. | |
| C8 | 190–250 | 110–175 | | | slow | 2–3 min. | |
| C9 | 200–205 | 260–290 | | | fast | 5–30 sec. | |
| C10 | 145 | 75 | | | fast | 5–30 sec | paste like/dries quick |
| C11 | 975 | 911 | | | fast | 5–30 sec | fine gelled particles |

Squalene and Olive oil were commercial samples used as purchased from chemical vendors. Oleo/milk is a mixture of Parkay™ Margarine and Carnation™ Instant Powdered Milk in a ratio of 70 parts/30 parts (in weight percent). Synthetic sebum was used as purchased from U.S. Test Fabrics Inc., PO Box 26, West Pittston, Pa. 18643, USA. Rates of oil absorption and time required for complete oil absorption were noted for each sample. In most cases the oil absorption capacity of the oil absorbing emulsion polymers E1–E9 was equal to or greater than control compounds currently used as oil absorbing materials. The exceptions are control materials C5 and C11, also known as Polytrap™ 6603 and a copolymer of lauryl methacrylate and ethylene glycol dimethacrylate, respectively. Both C5 and C11 exhibit high oil absorption capacities and are chemically related compositions, being highly cross-linked, porous copolymers that entrap oil within their porous polymer networks. Oil-absorbing emulsion polymers E1–E9 do not require high levels of cross-linking or any cross-linking to provide effective oil absorption as compared to C5 and C11. The mechanism of oil absorption for polymers E1–E9 is likely due to polymer swelling, as shown from microscopic analysis in contrast to oil entrapment in pores and voids of polymers C5 and C11.

TABLE IV

Comparison of Oil Absorption Values (OAV) vs Polymer Mass (g) for polymer compositions E1 and E4 for Squalene Absorption

| Mass in grams | Oil Absorption Value E1 | Oil Absorption Value E4 |
|---|---|---|
| 0.25 | 196 | 45 |
| 0.5 | | 60 |
| 1 | 286 | 71 |
| 2 | | 84 |

Table IV represents the oil absorption capacity of E1 and E4 after freeze drying the polymers. E4 has a much higher weight average molecular weight and correspondingly higher absorption capacity compared to E1. However, E1 forms a gelled complex, whereas E4 forms a smooth paste that is readily transferred from one surface to another surface/substrate.

Oil-Absorbing Emulsion Polymer Films

A series of polymer films were prepared by drying 1 g of an oil-absorbing polymer (50% solids) in a 2 ounce vial. Several types of oil samples (12 g) were added on top of the film and allowed to be absorbed into the polymer for a period of 20 days. The rate of oil absorption varies with a specific type of oil. Low molecular weight alkyl acrylates, such as LMA and SMA, showed substantial level of swelling within a day whereas swelling with Crisco oil and with Texaco motor oil showed much slower rate of swelling. The appearance of the swollen oil-containing polymer films have a gel like appearance while more hydrophilic polymers (e.g. E11) remain unchanged. Quantitative measurements were carried out by filtering the swollen oil-containing polymer film and free oil through a 100 mesh polypropylene filter and the weight of the swollen oil-containing films were determined. The % oil absorption was calculated based on the weight of oil absorbed by the film (0.5 g). The result indicated that hydrophobic, oil-absorbing polymers have the capacity to absorb a variety of oils while a hydrophilic E11 polymer showed no affinity to the oils tested. Moreover, cross-linking of the polymers reduced oil absorption levels (e.g. E13 and E14). See Table V.

TABLE V

Oil-absorption Data for Oil Absorbing Emulsion Polymer Films

| Example No. | Oil | Appearance | % Absorption |
|---|---|---|---|
| E11 (internal control) | SMA | Film | (1) |
| E11 (internal control) | LMA | Film | (1) |
| E11 (internal control) | Sunpar ™ 110N | Film | (1) |
| E11 (internal control) | Exxon ™ 1380 | Film | (1) |
| E11 (internal control) | Elefac ™ 1205 | Film | (1) |
| E11 (internal control) | Crisco ™ | Film | (1) |
| E11 (internal control) | Valvoline ™ Motor Oil | Film | (1) |
| E12 | LMA | Gel | 1850 |
| " | SMA | Gel | 1950 |
| " | Exxon ™ 1380 | Gel | 1310 |
| " | Sunpar ™ 110N | Gel | 970 |
| " | Elefac ™ 1205 | Gel | 1810 |
| " | Mazola ™ oil | Gel | 720 |
| " | Valvoline ™ Motor Oil | Gel | 330 |
| E1 | SMA | Gel | 1390 |
| " | Exxon ™ 1380 | Gel | 1370 |

TABLE V-continued

Oil-absorption Data for Oil Absorbing Emulsion Polymer Films

| Example No. | Oil | Appearance | % Absorption |
|---|---|---|---|
| " | Sunpar ™ 110N | Gel | 930 |
| " | Elefac ™ 1205 | Gel | 1430 |
| " | Valvoline ™ Motor Oil | Gel | 350 |
| E13 | SMA | Gel | 750 |
| " | Exxon ™ 1380 | Gel | 620 |
| " | Sunpar ™ 110N | Gel | 390 |
| " | Elefac ™ 1205 | Gel | 640 |
| " | Valvoline ™ Motor Oil | Gel | 460 |
| E14 | SMA | Gel | 630 |
| " | Exxon ™ 1380 | Gel | 570 |
| " | Sunpar ™ 110N | Gel | 470 |
| " | Elefac ™ 1205 | Gel | 590 |
| " | Valvoline ™ Motor Oil | Gel | 600 |

(1)No apparent absorption of oil into polymer film
Elefac ™ 1-205 (Bernel Chemical Co. Englewood, NJ 07631) is Octyl dodecyl Neopentanoate.
SMA is stearyl methacrylate monomer, LMA is Lauryl methacrylate monomer.
Crisco and Mazola Oil are standard cooking ingredients.

The process of oil-absorption using oil-absorbing polymers is reversible, since the swollen oil-containing polymer films can be transferred to another medium or substrate to transfer, transport or release the oil from the swollen oil-containing films. A multiphase, heterogeneous aqueous system can be described as Receptor/Water/Reservoir, wherein the receptor refers to a substrate upon which an oily substance or hydrophobic material is released, removed, deposited, transported or transferred through an aqueous phase, optionally using a complexation or phase transfer agent, from an oil-absorbing polymer and an oily substance or hydrophobic material, which refers to the reservoir. One embodiment is an oil-absorbing polymer film that absorbs an oily substance to become an oil-containing polymer film. The oil-containing film can then be used as prepared or may be formulated to prepare an oil-releasing polymer film, which releases the oily substance on to a substrate by several means including, but not limited to, mechanical force, osmotic pressure, diffusion, capillary action or a combination of the means. Another embodiment is an oil-absorbing polymer solid in the form of a powder or dispersion in water that swells upon contact with oil to result in a oil-containing polymeric solid. The solid is formulated and/or combined with a carrier that allows the release of an oily substance or hydrophobic material on to a substrate from the oil-containing polymer composition. In a reversible embodiment, an oil-absorbing polymer solid can be formulated or combined with a carrier to remove an oily substance or hydrophobic material from a substrate. The Receptor/Reservoir system makes use of the principle that a hydrophobic, oil-absorbing polymer composition will absorb like materials, such as oily substances or hydrophobic materials ("like absorbs like"). The process is reversible in that "like releases like" or "like transports like", so that the oil-containing polymer compositions can be prepared from the oil-absorbing compositions to release, transport or deposit an oily substance or hydrophobic material on to a substrate.

TABLE VI

Time Dependent Oil Absorption Values for Oil Absorbing Emulsion Polymer E1 vs Time

|  | E4 (instantaneous) | E1 (instantaneous) | E1 (several days) |
|---|---|---|---|
| Oil Absorption Value | 135 | 285 | 920 |

Table VI summarizes the time dependent oil absorption capacity of oil-absorbing emulsion polymer E1 in freeze dried form as compared to a oil-absorbing emulsion polymer film over time. In the form of a freeze dried powder having high surface area, E1 rapidly absorbs 3 times its own weight. In the form of a film and over an extended period of time, E1 can absorb cooking oil up to 10 times its weight.

Applications of Oil-absorbing Emulsion Polymers

The oil-absorbing polymer compositions of the present invention have utility in removing oily substances or hydrophobic materials ("like absorbs like") from fabrics and textiles by direct contact or in a washing cycle using 5 standard phosphate based detergents.

Laundry Test Protocol: Pre-treatment of Fabric By Direct Application Of Oil-Absorbing Polymers Prior to Soiling and Washing.

Cotton Fabric (3½"×4½"), purchased from TestFabrics, Inc. (West Pittston, Pa.), was treated with 0.5 g Rhodamine Dyed Squalene by delivery onto the center of the cloth using a pipette. The squalene was allowed to wick into the fabric overnight and subsequently air dried. The oil-absorbing polymer composition was applied onto the soiled cotton fabric by directly applying an aqueous neutralized polymer solution. The polymer wetted fabrics were then allowed to air dry. The polymer treated cloths were then laundered using the typical wash conditions as detailed in the table below:

TABLE VII

Wash Conditions

| Washing Apparatus: | United States Testing Company Terg-O-Tometer (Model 7243-S) |
|---|---|
| Wash Temperature | 25° C. |
| Water Hardness | 600 ppm (2/1 $Ca^{++}/Mg^{++}$) |
| Agitation | 100 rpm |
| Wash Cycle | 12 minutes |
| Rinse Cycle | 2 minutes |
| Water Capacity | 1 Liter |
| Detergent Concentration | 300 ppm |
| Polymer Concentration | 0.5 g of concentrate used as spot pretreatment |

TABLE VIII

Phosphate Powder Detergent

| Components | % by Weight |
|---|---|
| Linear Alkyl Benzene Sulfonate | 17.0 |
| Sodium Tripolyphospahte | 170 |
| Sodium Carbonate | 8.0 |
| Sodium Sulfate | 44.0 |
| Sodium Silicate | 10.0 |
| Carboxy Methyl Cellulose | 1.0 |
| Deionized Water/Misc.[1] | 3.0 |

[1]Miscellaneous includes optical brighteners, enzymes, chlorine scavengers, colorants, fragrance and opacifiers.

The reflectance of each cloth was measured using a Hunter Lab Colorimeter (ColorQUEST™ 45/0) and the data recorded using the X, Y and Z color scale. The Reflectance (Y) was usually measured before soiling so that only cloths of the same reflectance were used in a given test. Reflectance was then measured after laundering to evaluate the effectiveness of the polymer. The Whiteness Index values are the change in reflectance from unwashed to washed cloths.

TABLE IX

Whiteness Index for Oil-Absorbing Polymer E4,
Squalene Removal after one cycle, 300 ppm Phosphate Base, 600 ppm Hard Water

|  | Treated with E4 then washed | Without Polymer treatment then washed | Unwashed control |
|---|---|---|---|
| Whiteness Index | 67 | 37 | 38 |

Table IX summarizes whiteness index for an oil-absorbing polymer composition, E4. Cotton cloth was treated with Rhodamine dyed squalene (0.5 g), then air dried 16 hours. Oil-absorbing polymer was direct applied as an aqueous, neutralized solution of polymer, 0.5 g E4, onto center of cloths. The polymer wetted cloths were dried then laundered in a tergotometer using a 12 min. wash/2 min. rinse cycle. Laundered cloths were air dried and the reflectance was measured. The whiteness Index is an indicator of the amount of soil removed from the cloths. Cotton cloths treated with E4 oil absorbing polymer exhibited significantly enhanced squalene removal as compared to untreated cloths washed under the same laundering conditions. Moreover, untreated laundered cloths exhibited a similar whiteness index as the unwashed control, indicating no squalene was removed by the detergent.

As well as promoting the release of oily substances from surfaces, the present invention also provides the advantage in that it prevents build up of squalene and the subsequent oxidation of squalene that causes yellowing of fabrics with time. In a preferred embodiment of the present invention, the oil-absorbing polymer composition is also effective at promoting the release of oily substances from fabrics, especially cotton and cotton-containing fabrics.

TABLE X

Whiteness Index for Oil-Absorbing Polymer as a Function of Percentage of Polymer Solids and Dosage

|  | 1% E4 | 10% E4 | 25% E4 | 53% E4 | No Polymer |
|---|---|---|---|---|---|
|  | 0.1 g of | | | | |
| Whiteness Index | 41 | 43 | 43 | 55 | 32 |
|  | 0.25 g of | | | | |
| Whiteness Index | 42 | 39 | 42 | 60 | 32 |

Table X summarizes Whiteness Index data on polymer treated cloths as a function of the percent polymer solids and dosage of the oil-absorbing polymer E4. As the percentage of polymer solids increases for a particular dosage of oil-absorbing polymer, the squalene absorption markedly increases. At dilute concentrations of oil-absorbing polymer, squalene absorption appears to be independent of polymer dosage. All levels of oil-absorbing polymer, however, showed improved squalene absorption as compared to the control.

TABLE XI

Effects of Squalene Aging on Whiteness Index of an Oil-Absorbing Polymer

|  | No Polymer | E4 25% 0.5 g | E4 25% 0.25 g | E4 53% 0.5 g | E4 53% 0.25 g |
|---|---|---|---|---|---|
| Squalene 40 C. 16 hrs | −2 | 15.2 | 22.5 | 45.2 | 45.5 |
| Squalene 25 C. 16 hrs | 19.8 | 31 | 33.7 | 56.7 | 51 |

Table XI summarizes the effects of aging squalene on the whiteness index for the oil-absorbing polymer, E4. Squalene aging was accomplished by examining squalene treated cloth at two temperatures, 25° C. versus 40° C. for 16 hrs. The higher temperature would likely produced partially oxidized squalene in the cloth, making its removal more difficult. Removal of squalene from squalene aged cloths using the oil absorbing E4 polymer was observed, though at diminished levels as compared to squalene removal from cloths aged at 25° C.

TABLE XII

Laundry Pretreatment Data for Oil-Absorbing Polymers

|  | No Polymer | E1 | E7 | E8 | E4 | E2 | E3 | E10 | E9 |
|---|---|---|---|---|---|---|---|---|---|
| Polymer at 0.25 g | 1 | 1 | 1.25 | 3 | 4 | 2 | 3.5 | 1.5 | 2 |
| Polymer at 0.5 g | 1 | 1.25 | 2 | 3 | 4.5 | 3 | 4 | 1.5 | 2 |

The oil-absorbing polymer compositions of the present invention have utility in removing oily substances from glassware and ceramic, metal, and plastic tableware. The oil-absorbing polymers in this application were not directly applied to the soiled area of the tableware. Tableware was soiled using three types of oily or oil-based substances: a salad dressing, a barbeque sauce and a mixture of synthetic oils (cooking oil, lard, etc). The soiled tableware was allowed to stand overnight. An aqueous solution of an oil absorbing polymer (E1, E4 or E10, internal control) was added together with an automatic dish washing detergent (Cascade®). The concentration of oil absorbing polymer was 0.5%, based on 25 g of dish washing detergent. The table ware was washed at 35° C. through a normal wash/rinse cycle using water having a hardness level of 300 ppm $Ca^{2+}/Mg^{2+}$, 2:1. After the drying cycle the tableware was removed and evaluated by visual inspection to evaluate the removal of oily substances. A rating scale of 5 indicates complete removal and a rating of 0 indicates no removal.

TABLE XIII

Dish Washing Data for Oil-Absorbing Polymers

|  | Cascade | Cascade 0.5% E4 | Cascade 0.5% E10 | Cascade 0.5% E1 |
|---|---|---|---|---|
| French Dressing | 5 | 5 | 4.5 | 3.5 |
| Barbeque Sauce | 4.5 | 5 | 4 | 5 |
| Synthetic Mix | 3.5 | 4.5 | 3.5 | 2.5 |

Table XIII summarizes dish washing data in a single cycle soil removal test wash done in a Kenmore® dishwasher using Cascade® automatic dishwasher detergent. Post addition of the oil-absorbing polymer E4 in the wash bath enhances the removal of the barbeque sauce and the synthetic oily mixture as compared to the control.

The oil-absorbing polymer compositions of the present invention have utility as an additive to a floor cleaning composition. Ceramic black tiles were treated with a mixture of mud and motor oil. The soiled tiles were baked at 80° C. for 20 hours. Washing of tiles is performed with a Byk Gardner Abrasion Tester. Each solution is tested on 2 tiles. A washing solution (10 g) is deposited on a sponge and 10 passes (back and forth) are applied on the tiles. Washing solutions contain 10 g/Liter of a current detergent for hard surfaces (Mr. Proper™, Proctor and Gamble), an oil absorbing polymer containing 4% solids and enough tap water to make a 1 liter solution. Detergency is evaluated according to:

% Detergency Washed-Dirty/Clean-Dirty)×100 where washed, dirty and clean are average measurements made on the tiles.

Table XII summarizes a ranking for oil-absorbing polymers based on visual inspection of squalene removal. Squalene removal increased markedly as molecular weight decreased in the series of oil-absorbing polymers E1 to E4. Low molecular polymers E3 and E4 exhibited the largest squalene absorption levels. The same observation was noted in physical blends of oil-absorbing polymers containing E1 and E4, namely samples E7 and E8. As the weight % of E4 increased the squalene absorption increased. Comparative example E9 indicated that reduction of hydrophobic monomers in the oil-absorbing polymer resulted in diminished squalene absorption. Comparative example E10 indicated that incorporating smaller alkyl chains in the oil-absorbing polymer further diminishes squalene absorption. All oil-absorbing polymers performed better than the control.

TABLE XIV

Detergency Data for Oil-Absorbing Polymer in Floor Care

|  | Mr. Proper | Mr. Proper w/4% E1 | Mr. Proper w/4% E4 |
| --- | --- | --- | --- |
| % Detergency | 57.7 | 51.6 | 67.1 |

Table XIV summarizes the detergency of oil-absorbing polymers E1 and E4 in a floor cleaning composition. E4 exhibits effectiveness in removing an oily mixture as compared to the control.

TABLE XV

Hard Surface Cleaning Data for Oil-Absorbing Polymers

|  | No Polymer | E1 | E7 | E8 | E4 | E2 | E3 | E10 | E9 |
| --- | --- | --- | --- | --- | --- | --- | --- | --- | --- |
| Soil Removal | 3 | 21 | 3 | 3 | 4.5 | 4 | 4.5 | 3.5 | 3.5 |

Table XV summarizes hard surface cleaning data for a number of oil-absorbing polymers. Ceramic tiles were treated with French dressing and subsequently air dried for 16 hrs. Samples were placed in Byk Gardener Abrasion Tester and sponge was treated with 5 g Fantastic® cleanser without polymer (control) and containing polymer at 3% solids level. Test machine was run for 10 cycles then tiles were removed and rated for soil removal. Oil-absorbing polymer compositions having the lowest weight average molecular weights (E3 and E4) exhibited the highest effectiveness in removing the oily substance.

The oil-absorbing polymer compositions of the present invention have utility in removing oily substances from surfaces such as skin. As a model for human skin, artifical skin was used in the analysis. Artificial skin in sheets was hydrated in glycerol water mixture then treated with synthetic sebum oil mixture. Synthetic sebum is a mixture of triglycerides, waxy esters, fatty acids, squalene, diglycerides, cholesterol esters and cholesterol, as described by D. T. Downing in the publication, Journal of Investigative Dermatology, Volume 53, page 322, 1969. The oil-absorbing polymers E1, E4 and E10 were added to Oil of Olay® Body wash at a 0.5% solids level, then rubbed on to the soiled artificial skin for a period of 10 seconds, and rinsed off using tap water. The sheets were visually inspected to evaluate removal of the synthetic sebum from the artificial skin.

TABLE XVI

Skin Cleansing Data for Oil-Absorbing Polymers

|  | Oil Of Olay | Oil of Olay w/E4 | Oil of Olay w/E1 | Oil of Olay w/E10 |
| --- | --- | --- | --- | --- |
| Synthetic Sebum Removal | 2.75 | 4.5 | 2.5 | 2.5 |

Table XVI summarizes skin cleansing data for three oil-absorbing polymers. A rating of 5 equals complete removal and 0 represents no removal. Oil-absorbing polymer E4 removed more of the synthetic sebum than the control, E1 or E10.

We claim:

1. An oil-absorbing composition that absorbs at least 20 weight percent of at least one oily substance including hydrophobic material in a heterogeneous medium, based on the total weight of the composition, comprising an aqueous emulsion polymer having as polymerized monomer units: (a) from 1 to 3% by weight of at least one inonic monomer selected from acrylic acid and methacrylic acid (b) from 90 to 95% by weight of at least one $C_{12}$–$C_{20}$ alkyl (meth) acrylate and (c) form 0 to 5% by weight of at least one $C_1$–$C_4$ (methacrylate; the emulsion polymer having a glass having a Tg of 25° C. or less.

2. The oil-absorbing composition of claim 1, wherein the ionic monomer is (meth)acrylic acid and wherein the $C_{12}$–$C_{20}$ alkyl (meth)acrylate monomers are selected from the group consisting of lauryl acrylate, lauryl (meth)acrylate (LMA), oleyl (meth)acrylate, palmityl (meth)acrylate, stearyl (meth)acrylate (SMA), cetyl(meth)acrylate, eicosyl (meth)acrylate, blends of $C_{12}$–$C_{20}$ alkyl (meth)acrylates, cetyl-eicosyl (meth)acrylate (CEMA); aromatic and alkyl aromatic esters of (meth)acrylic acid, unsaturated vinyl esters of (meth)acrylic acid derived from fatty acids and fatty alcohols and combinations thereof; and wherein $C_1$–$C_4$ (meth)acrylate is methyl(meth)acrylate.

3. The oil-absorbing composition of claim 1, the aqueous emulsion polymer having a weight average molecular weight ranging from 1000 to 600,000.

4. The oil-absorbing composition of claim 1, wherein the oil-absorbing composition is combined with at least one oily substance including hydrophobic material to produce an oil-containing composition, that is capable of releasing at least some amount of the oily substance including hydrophobic materials on to a substrate.

5. The oil-absorbing composition of claim 4, wherein the oil-absorbing composition is in the form of a solid or liquid selected from the group consisting of spray dried powders, freeze dried powders, granules, films, water-borne latex dispersions and combinations thereof.

6. The oil-absorbing composition of claim 4, wherein the oil-absorbing composition includes a carrier.

7. The oil-absorbing composition of claim 1, wherein the oily substance including hydrophobic materials is selected from the group consisting of body oils, sebum, squalene, proteins, protein containing substances, food, blood, fat, fatty acids, waxes, mineral oils, silicone oils, motor oils, crude oils, organic compounds, lipophilic toxins, pesticides, insecticides, herbicides, greases, vegetable oils and combinations thereof; wherein the substrate is selected from the group consisting of textiles, fabric, hard surfaces, ceramics, wood, tile asphalt, cement, skin and combinations thereof; and wherein the carrier is selected from the group consisting of plastics sheets, cosmetic strips, fibers, textiles, filter materials, paper products, inorganic solids, detergents, cleaners, soaps and combinations thereof.

8. A process for removing an oily substance including hydrophobic materials from a substrate in a heterogeneous medium comprising the steps of:
  directly contacting the oily substance or hydrophobic material on the substrate with an oil-absorbing composition that comprises an aqueous emulsion polymer having as polymerized monomer units: (a) from 1 to 3% by weight of at least one ionic monomer selected from acrylic acid and methacrylic acid (b) from 90 to 95% by weight of at least one $C_{12}$–$C_{20}$ alkyl (meth)acrylate and (c) from 0 to 5% by weight of at least one $C_1$–$C_4$ (meth)acrylate; the emulsion polymer having a glass having a Tg of 25° C. or less to absorb the oily substance or hydrophobic material;
  and removing the swollen oil-containing polymer composition from the substrate and the medium.

9. The process according to claim 8, wherein the process is reversible.

10. The process according to claim 9, wherein the ionic monomer is (meth)acrylic acid and wherein the hydrophobic monomers are selected from the group consisting of $C_{12}$–$C_{20}$ alkyl (meth)acrylates, lauryl acrylate, lauryl (meth)acrylate (LMA), oleyl (meth)acrylate, palmityl (meth)acrylate, stearyl (meth)acrylate (SMA), cetyl(meth)acrylate, eicosyl(meth)acrylate, blends of $C_{12}$–$C_{20}$ alkyl (meth)acrylates, cetyl-eicosyl (meth)acrylate (CEMA); aromatic and alkyl aromatic esters of (meth)acrylic acid, unsaturated vinyl esters of (meth)acrylic acid derived from fatty acids and fatty alcohols and combinations thereof; and wherein the $C_1$–$C_4$ (meth)acrylate is methyl(meth)acrylate.

11. The process according to claim 10, the aqueous emulsion polymer having a weight average molecular weight ranging from 1000 to 600,000.

12. The process according to claim 8, wherein the oil-absorbing composition is in the form of a solid or liquid selected from the group consisting of spray dried powders, freeze dried powders, granules, films, water-borne latex dispersions and combinations thereof.

13. The process according to claim 12, wherein the oily substance or hydrophobic material is selected from the group consisting of body oils, sebum, squalene, proteins, protein containing substances, food, blood, fat, fatty acids, waxes, mineral oils, silicone oils, motor oils, crude oils, organic compounds, lipophilic toxins, pesticides, insecticides, herbicides, greases, vegetable oils and combinations thereof; wherein the substrate is selected from the group consisting of textiles, fabric, hard surfaces, ceramics, wood, tile asphalt, cement, skin and combinations thereof; and wherein the carrier is selected from the group consisting of plastics sheets, cosmetic strips, fibers, textiles, filter materials, paper products, inorganic solids, detergents, cleaners, soaps and combinations thereof.

14. A process for removing an oily substance including hydrophobic materials in a heterogeneous medium comprising the steps of; combining a substrate containing an oily substance, an oil-absorbing polymer composition, wherein the oil-absorbing composition comprises an aqueous emulsion polymer having as polymerized monomer units: (a) from 1 to 3% by weight of at least one ionic monomer selected from acrylic acid and methacrylic acid (b) from 90 to 95% by weight of at least one $C_{12}$–$C_{20}$ alkyl (meth)acrylate and (c) from 0 to 5% by weight of at least one $C_1$–$C_4$ (meth)acrylate; the emulsion polymer having a glass having a Tg of 25° C. or less; and, optionally, a complexation agent to facilitate transport in the medium, wherein the oil-absorbing composition absorbs at least 20 weight percent of at least one oily substance or at least one oily substance or at least one hydrophobic material in a heterogeneous medium, based on the total weight of the polymer composition; allowing the composition to absorb the oily substance or hydrophobic material; and separating the swollen oil-containing polymer composition from the medium.

15. The process according to claim 14, wherein the process is reversible.

16. The process according to claim 15, wherein the ionic monomer is (meth)acrylic acid and wherein the hydrophobic monomers are selected from the group consisting of $C_1$–$C_{24}$ alkyl acrylates, $C_1$–$C_{24}$ alkyl (meth)acrylates, methyl(meth)acrylate, ethyl acrylate (EA), isopropyl (meth)acrylate, butyl acrylate(BA), butyl (meth)acrylate (BMA), 2-ethyl hexyl acrylate, benzyl (meth)acrylate, octyl acrylate, decyl acrylate, lauryl acrylate, lauryl (meth)acrylate (LMA), oleyl (meth)acrylate, palmityl (meth)acrylate, stearyl (meth)acrylate (SMA), cetyl(meth)acrylate, eicosyl(meth)acrylate, blends of $C_{10}$–$C_{24}$ alkyl (meth)acrylates, cetyl-eicosyl (meth)acrylate (CEMA); aromatic and alkyl aromatic esters of (meth)acrylic acid, unsaturated vinyl esters of (meth)acrylic acid derived from fatty acids and fatty alcohols and combinations thereof; and wherein the $C_1$–$C_4$ (meth)acrylate is methyl(meth)acrylate.

17. The process according to claim 16, the aqueous emulsion polymer having a weight average molecular weight ranging from 1000 to 600,000.

18. The process according to claim 14, wherein the composition is in the form of a solid or liquid selected from the group consisting of spray dried powders, freeze dried powders, granules, films, water-borne latex dispersions and combinations thereof.

19. The process according to claim 18, wherein the oily substance or hydrophobic material is selected from the group consisting of body oils, sebum, squalene, proteins, protein containing substances, food, blood, fat, fatty acids, waxes, mineral oils, silicone oils, motor oils, crude oils, organic compounds, lipophilic toxins, pesticides, insecticides, herbicides, greases, vegetable oils and combinations thereof; wherein the substrates are selected from the group consisting of textiles, fabric, hard surfaces, ceramics, wood, tile asphalt, cement, skin and combinations thereof; and wherein the carriers are selected from the group consisting of plastics sheets, cosmetic strips, fibers, textiles, filter materials, paper products, inorganic solids, detergents, cleaners, soaps and combinations thereof.

* * * * *